(12) United States Patent
Gong et al.

(10) Patent No.: US 10,377,953 B2
(45) Date of Patent: Aug. 13, 2019

(54) FLUIDIZED UPGRADING/HYDROSTABILIZING OF PYROLYSIS VAPORS

(71) Applicant: PHILLIPS 66 COMPANY, Houston, TX (US)

(72) Inventors: Kening Gong, Bartlesville, OK (US); Liang Zhang, Owasso, OK (US); John R. Copeland, Tulsa, OK (US); Reed J. Eisenhart, Tulsa, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 15/807,267

(22) Filed: Nov. 8, 2017

(65) Prior Publication Data
US 2018/0127657 A1    May 10, 2018

Related U.S. Application Data (60) Provisional application No. 62/419,807, filed on Nov. 9, 2016, provisional application No. 62/419,815, filed on Nov. 9, 2016.

(51) Int. Cl.
| | | |
|---|---|---|
| C10B 53/02 | (2006.01) | |
| B01D 3/14 | (2006.01) | |
| C10G 7/02 | (2006.01) | |
| C10G 7/04 | (2006.01) | |
| C10G 45/02 | (2006.01) | |
| C10G 55/04 | (2006.01) | |
| C10G 3/00 | (2006.01) | |
| G01N 30/02 | (2006.01) | |

(52) U.S. Cl.
CPC .............. *C10B 53/02* (2013.01); *B01D 3/148* (2013.01); *C10G 3/57* (2013.01); *C10G 7/02* (2013.01); *C10G 7/04* (2013.01); *C10G 45/02* (2013.01); *C10G 55/04* (2013.01); *B01D 2257/702* (2013.01); *B01D 2257/80* (2013.01); *C10G 2300/104* (2013.01); *C10G 2300/1014* (2013.01); *C10G 2300/1044* (2013.01); *C10G 2300/1048* (2013.01); *G01N 2030/025* (2013.01); *Y02E 50/14* (2013.01); *Y02P 30/20* (2015.11)

(58) Field of Classification Search
CPC .......... B01D 2257/702; B01D 2257/80; B01D 3/148; C10B 53/02; C10G 2300/1014; C10G 2300/104; C10G 2300/1044; C10G 2300/1048; C10G 45/02; C10G 55/04; C10G 7/02; C10G 7/04
See application file for complete search history.

(56) References Cited

U.S. PATENT DOCUMENTS

2010/0251600 A1*  10/2010  Marker .................... C01B 3/16
                                                    44/308
2015/0073181 A1*  3/2015  Gorke .................... C10G 1/002
                                                    585/240

* cited by examiner

*Primary Examiner* — Sharon Pregler
(74) *Attorney, Agent, or Firm* — Phillips 66 Company (57) ABSTRACT

The present disclosure relates to processes and systems that convert biomass to stable intermediate hydrocarbon products that having a greatly decreased oxygen content. This stabilized intermediate hydrocarbon product may be easily be stored for an extended period of time, further refined into liquid transportation fuels (either alone or mixed with petroleum-derived hydrocarbons), or blended with petroleum-derived blendstocks to produce a finished liquid transportation fuel.

14 Claims, 4 Drawing Sheets

FLUIDIZED UPGRADING/HYDROSTABILIZING OF PYROLYSIS VAPORS

CROSS-REFERENCE TO RELATED APPLICATIONS

This application is a non-provisional application which claims the benefit of and priority to U.S. Provisional Application Ser. No. 62/419,807 and U.S. Provisional Application Ser. No. 62/419,815 both filed on Nov. 9, 2016, and both titled "Fluidized Upgrading/Hydrostabilizing of Pyrolysis Vapors". Each of these applications is hereby incorporated by reference.

STATEMENT REGARDING FEDERALLY SPONSORED RESEARCH OR DEVELOPMENT

None.

FIELD OF THE INVENTION

This invention relates to fast pyrolysis of organic matter into pyrolysis vapors, and the further conversion of the pyrolysis vapors to useful chemical or liquid fuel products.

BACKGROUND

Conventional fast pyrolysis of biomass entails rapid heating of a biomass feedstock in a hypoxic environment to produce a combination of non-condensable gases (C1-C4), condensable pyrolysis vapors and solid carbonaceous char. Condensation of the pyrolysis vapors produces a pyrolysis oil that is thermally unstable at temperatures relevant for traditional refinery process, which makes it use as a refinery feedstock potentially problematic. Pyrolysis oil instability is largely due to a high concentration of oxygenates as well as reactive functional groups that are predisposed to form polymers such as oligosaccharides and phenolic resins. The presence of particulates (such as, for example char) comprising adsorbed metals may also contribute to instability.

Conventional catalytic pyrolysis (either in-situ or ex-situ) processes can produce partially deoxygenated products that are more easily upgraded. However, these processes utilize conditions and catalysts that favor non-selective deoxygenation (cracking of both C—O and C—C bonds), leading to coke formation on the upgrading/hydrostabilizing catalyst. Consequently, these processes suffer from low organic liquid yield and short catalyst life, and typically require a regenerator to oxidize the coke and restore catalytic activity. Further, due to the relatively low pressure environment and nonselective chemistry, the pyrolysis vapor or condensed pyrolysis oil products of these processes are not fully stable and require additional upgrading/hydrostabilizing (i.e., hydrotreatment) to decrease reactivity of remaining reactive functional groups within the products. This has proven to be a major barrier to commercial implementation of pyrolysis technology.

Conventional non-catalytic fast pyrolysis of biomass typically mixes biomass with a heated solid particles (i.e., "heat carrier") to facilitate rapid heating of the biomass to a temperature ranging from 315° C. to 600° C. The resulting thermal-cracking of the heated feedstock produces non-condensable light gases, a solid carbonaceous char, and condensable pyrolysis vapors that can be converted to biofuels, or a component thereof.

Certain conventional processes for the pyrolysis of biomass upgrade pyrolysis vapors with a fixed bed hydrotreating reactor. Petroleum hydroprocessing technologies mainly use fixed bed reactors or, in few cases, ebulliated bed reactors. These reactors are good for petroleum feedstocks that normally contain less than 10 wt % of heteroatoms (O, S, N, etc.). However, the pyrolysis intermediates from biomass contain more than 30 wt % of oxygen and a large percentage of molecules containing unsaturated C—C bonds. Removing this oxygen and saturating these C—C double bonds releases much more heat that is extremely difficult to dissipate from a fixed bed reactor. Consequent over-reacting and local over-heating rapidly deactivates the beginning portion of the fixed bed reactor and eventually plugs the reactor. In addition, many conventional biomass pyrolysis methods inefficiently utilize multiple stages of hydrotreatment to convert the pyrolysis vapors to a stable liquid hydrocarbon product.

Certainly, there is a need to improve fast pyrolysis technology to facilitate the commercial-scale catalytic upgrading/hydrostabilizing of biomass-derived primary pyrolysis vapors into products that are fungible with current petroleum-derived liquid hydrocarbon fuels, or a component thereof.

BRIEF SUMMARY OF THE DISCLOSURE

Certain embodiments of the present disclosure comprise a process for pyrolyzing biomass and upgrading/hydrostabilizing the vapors, comprising: a) pyrolyzing a feedstock that is derived from biomass in a first reactor in the presence of a heavy stabilized hydrocarbon fraction consisting of molecules characterized by a boiling point (at 1 atm.) that is greater than 321° C., to produce a primary pyrolysis product comprising condensable pyrolysis vapors and char; b) conveying the condensable pyrolysis vapors to a second reactor containing hydrogen and at least one fluidized bed of at least one catalyst, and contacting the primary gaseous product with the at least one catalyst at conditions of temperature that facilitate the production of a stabilized hydrocarbon product, wherein the stabilized hydrocarbon product comprises hydrocarbons having less than 0.1 wt. percent aldehyde functional groups and less than 0.1 wt percent carboxylic acid functional groups; c) fractionating the stabilized hydrocarbon product to produce the heavy stabilized hydrocarbon fraction of a), and fuel-range stabilized hydrocarbons characterized by a boiling point ranging from between 25° C. and 321° C. In certain embodiments, the fractionating of part c) comprises selective condensation of the heavy stabilized fraction.

In certain embodiments, the fuel-range stabilized hydrocarbons comprises a light stabilized hydrocarbon fraction characterized by a boiling point ranging from between 25° C. and 193° C., and a medium stabilized hydrocarbon fraction characterized by a boiling point ranging from between 193° C. and 321° C.

In certain embodiments, the heavy stabilized hydrocarbon fraction consists of constituent molecules that boil above 321° C. In certain embodiments, the boiling point of at least 90 wt % of hydrocarbon molecules in the heavy stabilized hydrocarbon fraction is greater than 343° C., alternatively greater than 370° C. In certain embodiments, the boiling point of at least 90 wt % of hydrocarbon molecules in the heavy stabilized hydrocarbon fraction is in the range between 343° C. and 566° C., alternatively in the range between 350° C. and 500° C.

In certain embodiments, the process further comprises co-feeding the light stabilized hydrocarbon fraction, the medium stabilized hydrocarbon fraction, or both, with petroleum-derived hydrocarbons to a refinery process.

In certain embodiments, the process further comprises condensing and storing the light stabilized hydrocarbon fraction, the medium stabilized hydrocarbon fraction, or both, for a period in excess of seven days prior to use.

In certain embodiments, the process further comprises blending the light stabilized hydrocarbon fraction, the medium stabilized hydrocarbon fraction, or both, with conventional petroleum-derived hydrocarbons to produce a finished liquid transportation fuel.

In certain embodiments, recycling of the heavy stabilized hydrocarbon fraction to the pyrolysis reactor decreases the partial pressure of hydrogen required in the second reactor by at least 50 psig.

The present disclosure also describes a system for the production and upgrading/hydrostabilizing of a stabilized pyrolysis product, comprising: a) a pyrolysis reactor configured to fluidize and rapidly pyrolyze a feedstock comprising biomass for a residence time of between 1 and 20 seconds to produce a gaseous product comprising non-condensable light gases, condensable pyrolysis vapors, and char, wherein the pyrolysis reactor comprises a first inlet configured to receive a stabilized heavy hydrocarbon fraction comprising stabilized hydrocarbons that are characterized by a boiling point greater than 350° C., a second inlet configured to receive the biomass feedstock, at least one outlet configured to remove the gaseous product from the reactor, at least one inlet configured to receive a carrier gas and operable to fluidize the feedstock; b) a second reactor containing at least one catalyst in a fluidized bed configuration, wherein the second reactor is configured to receive the gaseous product and maintain a temperature and pressure that facilitate the catalytic conversion of the condensable pyrolysis vapors to produce a stabilized hydrocarbon product; c) a fractionation device configured to separate the stabilized hydrocarbon product to produce a heavy stabilized hydrocarbon fraction, the fractionation further comprising an outlet for the heavy stabilized hydrocarbon fraction; d) a conduit operably connected to receive the heavy stabilized hydrocarbon fraction and convey it to the pyrolysis reactor.

In certain embodiments of the system, the pyrolysis reactor additionally comprises a fluidizable bed of a heat carrier, the heat carrier comprising a particulate solid.

In certain embodiments of the system, the pyrolysis reactor is configured to pyrolyze the biomass feedstock at a temperature in the range from 300° C. to 650° C. and for a residence time of less than 10 sec.

In certain embodiments of the system, the second reactor comprises a fluidized bed of at least one upgrading/hydrostabilizing catalyst, wherein the second reactor is configured to catalytically convert produce a stabilized hydrocarbon product that is suitable for use as a member selected from the list consisting of: a co-feed for a conventional refinery process, a liquid hydrocarbon transportation fuel or a component thereof.

Certain embodiments of the system further comprise a separator that is directly coupled to the second reactor and configured to receive the stabilized hydrocarbon product from the second reactor and to remove water and flue gas from the stabilized hydrocarbon product to produce a dewatered stabilized hydrocarbon product.

Certain embodiments of the system further comprise a fractionation device that is directly coupled to the separator and configured to receive the dewatered stabilized hydrocarbon product from the separator, wherein the fractionation device is configured to receive and fractionate the dewatered stabilized hydrocarbon product into two or more fractions based upon boiling point, wherein the fraction

BRIEF DESCRIPTION OF THE DRAWINGS

A more complete understanding of the present invention and benefits thereof may be acquired by referring to the follow description taken in conjunction with the accompanying drawings in which.

The invention is susceptible to various modifications and alternative forms, specific embodiments thereof are shown by way of example in the drawings. The drawings may not be to scale. It should be understood that the drawings and their accompanying detailed descriptions are not intended to limit the scope of the claimed invention to the particular embodiments illustrated.

DETAILED DESCRIPTION

The present disclosure relates to processes and systems that convert biomass to stable intermediate hydrocarbon products that having a greatly decreased oxygen content. This stabilized intermediate hydrocarbon product may be easily be stored for an extended period of time, further refined into liquid transportation fuels (either alone or mixed with petroleum-derived hydrocarbons), or blended with petroleum-derived blendstocks to produce a finished liquid transportation fuel. In its simplest form, the process involves: 1) co-pyrolysis of biomass along with a recycled heavy stabilized hydrocarbon fraction that is derived from the process to form pyrolysis vapors possessing improved upgradability, and; 2) catalytically upgrading/hydrostabilizing and/or stabilizing the pyrolysis vapors in a fluidized bed comprising at least one upgrading/hydrostabilizing catalyst, wherein the upgrading/hydrostabilizing selectively cracks C—O bonds of oxygenates present in the pyrolysis vapors to remove oxygen while maintaining C—C backbones. The resulting products possess a lower oxygen content, is thermally stable and may be 1) stored, 2) upgraded further in a commercial refinery, or 3) blended with petroleum derived hydrocarbon fractions to produce a liquid transportation fuel.

The processes and systems disclosed herein hydrodeoxygenate the pyrolysis vapors in a single fluidized upgrading/hydrostabilizing step, which is superior to many conventional biomass pyrolysis methods that utilize multiple stages of hydrotreatment to convert the pyrolysis vapors to a stable liquid hydrocarbon product. Thus, the instant overall process is more efficient and requires reduced capital expenditure to implement.

The inventive processes and systems described herein pyrolyze a biomass feedstock in a reactor that is maintained at a temperature that facilitates rapid heating and pyrolysis of the biomass, utilizing for a relatively short residence time for the feedstock in the reactor of less than 1 min, optionally less than 30 sec, optionally less than 10 sec, optionally less than 5 sec, optionally less than 2 sec, optionally less than 1 sec. As the biomass feedstock pyrolyzes in the pyrolysis reactor, a pyrolysis product forms comprising non-condensable light gases, condensable pyrolysis vapors, and char. A heated carrier gas (optionally, a reactive gas) may be used to assist in fluidizing the biomass feedstock and separating the non-condensable light gases, condensable pyrolysis vapors, and char from the heat carrier. After removing the char, the non-condensable light gases and condensable pyrolysis vapors quickly move into a second reactor comprising at least one upgrading/hydrostabilizing or stabilizing catalyst in a fluidized bed configuration.

The pyrolysis reactor can be of any suitable design to assure rapid heating and pyrolysis of the biomass, such as a fluidized bed reactor, rotation cone reactor, rising circulating reactor, auger reactor, or other suitable design. The pyrolysis temperature typically ranges from 300° C. to 600° C. Certain embodiments utilize a particulate heat carrier in the first pyrolysis stage that assists in rapidly and evenly distributing heat to the biomass feedstock, which assist rapid thermal cracking of the feedstock to produce oxygenated hydrocarbon vapors. However, the temperature within the pyrolysis reactor first stage may be maintained via one or more of the following mechanisms, including (but not limited to) addition of a heated solid particulate heat carrier, adding a pre-heated biomass feedstock, addition of a heated carrier gas, heating of the reactor walls utilizing heating elements located either external or internal to the pyrolysis reactor, microwave or inductive heating, addition of a heated recycled fraction of the stabilized product, or any other heating mechanism known in the art.

In certain embodiments, the pyrolysis reactor is a fluidized bed reactor containing a solid particulate heat carrier. With proper fluidization conditions, biomass-derived char can be separated from the heat carrier due to density difference, then entrained in the fluidizing carrier gas leaving the reactor. Entrained char is then separated from the pyrolysis vapor by conventional means (such as, for example, a solid-gas separation device such as cyclone) before the cleaned vapor flows into the upgrading/hydrostabilizing reactor containing at least one fluidized bed of upgrading/hydrostabilizing catalyst (such as, for example, a hydrotreating catalyst on a fluidizable support). Separation of char also prevents contamination of the catalyst with metals, thereby potentially increasing the catalyst lifetime, because most of metals present in biomass become associated with the char. Data on enrichment of metals in char is found in prior patent application publication US 2014/0069012, which is incorporated herein by reference.

The stream of carrier gas may be utilized to: 1) fluidize the biomass feedstock and particulate heat carrier, 2) assist in moving the produced pyrolysis vapors out of the reactor, 3) react with the produced pyrolysis vapors to decrease reactivity and coke formation, or combinations thereof. In certain embodiments, the carrier gas comprise one or more of many gases that are either inert or reactive. For example, the carrier gas may comprise gases such as nitrogen, helium, argon, hydrogen, methane, light hydrocarbons, flue gas and mixtures thereof. If the carrier gas comprises a reactive gas, the reactive gas may optionally react with the biomass during pyrolysis, may serve as a reactant when the pyrolysis products are upgraded by contacting the upgrading/hydrostabilizing catalyst(s), or both. The carrier gas may be injected into the system at more than one point, or injected simultaneously at multiple points. One point may comprise combining the carrier gas with the feedstock prior to entering the pyrolysis reactor, while another may comprise injecting carrier gas directly into the pyrolysis reactor proximal to the biomass feedstock inlet. A third point may comprise injecting the carrier gas proximal to the first outlet of the pyrolysis reactor.

The volumetric flow rate, or "standard gas hourly space velocity" (SGHSV) of the carrier gas is adjusted to minimize the time between pyrolysis and catalytic upgrading/hydrostabilizing, such that the upgrading/hydrostabilizing catalyst (or optionally, catalysts) contacts primary products of pyrolysis and not secondary pyrolysis products that comprise 16 or more carbons and are more difficult to upgrade to a bio-derived fuel. Volumetric flow rate for a given embodiment depends upon factors including, but not limited to, the volume of the pyrolysis reactor, the temperature and pressure at which the pyrolysis reactor is maintained, the feed rate of the biomass feedstock to the pyrolysis reactor, and the type of feedstock utilized. The literature provides many examples of how these variables can be adjusted to determine an optimal volumetric flow rate for a desired pyrolysis outcome, including, for example, the pyrolysis liquid to pygas ratio, and the relative percentage of the feedstock converted to char. Thus, such methods will not be reiterated here.

Once formed, the pyrolysis vapors (optionally, stabilized pyrolysis vapors) are separated from the majority of produced solids comprising un-pyrolyzed feedstock, char, heat carrier (and metals largely associated with the char and heat carrier). The pyrolysis vapors are rapidly swept upward and out of the pyrolysis reactor via at least one outlet that is preferably at (or near) the top of the reactor. Any remaining entrained particulates may optionally be removed from the pyrolysis vapors by conventional methods and systems to prevent catalyst coking, fouling, poisoning or any combination of these.

In certain embodiments, such conventional methods and systems may include passing the pyrolysis vapors and any entrained residual particulates to a gas-solid separator, typically a cyclone, where the solids, mainly pyrolysis char, are separated from the pyrolysis vapors to produce particulate-free vapors. Most of the impurities that negatively impact the performance of upgrading/hydrostabilizing catalysts are associated with the char or entrained solids. Thus, separating the solids in a gas-solid separator to produce particulate-free vapors can help extend the catalyst lifetime.

The pyrolysis vapors (optionally cleaned and stabilized), leaving the pyrolysis reactor are fed into an upgrading/hydrostabilizing reactor comprising a fluidized bed comprising at least one upgrading/hydrostabilizing catalyst. Exemplary catalysts are discussed in more detail herein, but are generally provided on fluidizable, attrition resistant supports. The at least one upgrading/hydrostabilizing catalyst may be any known fluidizable catalyst capable of partly or fully converting the condensable pyrolysis vapors to a commercially acceptable liquid transportation fuel or a refinable intermediate. In certain embodiments, the at least one catalyst may hydrogenate and/or deoxygenate the gaseous pyrolysis products.

The upgrading/hydrostabilizing reactor comprises at least one upgrading/hydrostabilizing catalyst in a fluidized bed configuration. Preferably, the fluidized bed is self-contained and does not require periodic regeneration either in situ or by removing the catalyst. Though not preferred, the catalyst may still be periodically removed from the upgrading/hydrostabilizing reactor and passed through a regenerator for de-coking as needed, then returned to the pyrolysis reactor. Alternatively, fresh catalyst may be added on a periodic or continuous basis to the pyrolysis reactor to account for catalyst attrition and/or deactivation over time.

In certain embodiments, each fluidized catalyst bed may comprise mixtures of one or more catalysts of the types described above. Optionally, multiple catalyst beds may be placed within a single reactor, or multiple catalyst beds may be placed in different reactors to facilitate different reaction conditions. When multiple reactors are utilized, they may be arranged to either in parallel or series.

If multiple upgrading/hydrostabilizing reactors are utilized, different conditions may be maintained in each reactor in order to facilitate a given catalytic reaction. To facilitate flow of the vapors through multiple reactors, a pressure differential may be maintained wherein the pressure in each successive reactor progressively decreases.

The residence time of the pyrolysis vapors in each upgrading/hydrostabilizing reactor generally ranges from 0.01 sec to 1000 sec. preferably, the residence time is in a range from 0.05 sec to 400 secs. More preferably, the residence time is in a range from 0.1 sec to 200 sec. Most preferably, the residence time is in a range from 0.1 sec to 10 sec.

Conditions for upgrading/hydrostabilizing of the condensable pyrolysis vapors (e.g., temperature, pressure, choice of catalyst) are chosen to favor highly-selective cracking of C—O bonds, while preserving C—C bonds of the oxygenates in the vapor, and typically include temperatures in the range from 300-450° C. and pressures in the range from 200-500 psig.

The temperature maintained within each upgrading/hydrostabilizing reactor is generally in the range from 25° C. to 800° C. Preferably, the temperature is in the range from 180° C. to 600° C., although if multiple upgrading/hydrostabilizing reactors are used, each may be maintained at a different temperature within this range. Certain upgrading/hydrostabilizing reactions are advantageously conducted at a pressure that is greater than atmospheric pressure. The pressure that is maintained in the one or more upgrading/hydrostabilizing reactors may range from 0-3000 psig, although a preferred pressure range is zero to 1000 psig. In certain embodiments, the pressure may range from 10 to 800 psig, from 20 to 650 psig, from 100 to 500 psig, from 100 psig to 400 psig, from 200 psig to 400 psig, or from 250 to 350 psig. An exemplary pressure might be 250 psig, 300 psig, 350 psig, or 400 psig.

The flow of gas and vapors within each fluidized upgrading/hydrostabilizing reactor is preferably upward. Upon exiting the final upgrading/hydrostabilizing reactor, the upgraded gas and/or vapors are directed to a selective condensation system that functions to reduce the temperature of upgraded product vapors to a temperature that is at or below the dew point for at least one component. Typically, the conditions utilized do not result in the condensation of methane, but preferably will condense C4+ hydrocarbons.

Hydrogen may be separated from the uncondensed gas by a variety of conventional methods and recycled as at least a portion of the carrier gas. In certain embodiments, the recycled hydrogen may be added directly into, or just upstream from, an upgrading/hydrostabilizing reactor to facilitate one or more upgrading/hydrostabilizing reactions. Alternatively, the entirety, or some fraction, of the bulk non-condensable gas is used for the same purpose. In another embodiment, the entirety, or some fraction, of the bulk of the non-condensable gas is sent to a combustor or hydrogen generation unit (e.g., a reformer) to generate either heat or hydrogen, respectively. The resulting heat or hydrogen may then be partially or entirely recycled back to either the pyrolysis reactor.

The upgrading/hydrostabilizing reactor produces an upgraded, stabilized hydrocarbon product that is subsequently cooled, condensed and sent to a phase separator where an organic liquid phase is separated from any water and/or flue gas formed during pyrolysis or subsequent upgrading/hydrostabilizing. The organic liquid phase comprises mainly hydrocarbons and a small amount of oxygen (from less than 1 wt % to 10 wt %). Unlike conventional pyrolysis oil or even some catalytic pyrolysis oil that are extremely unstable, the organic liquid product is thermally stable.

The stabilized product is passed to a fractionator to be divided into three fractions based upon boiling point range: light stabilized hydrocarbon fraction (boiling point in the gasoline-range), medium stabilized hydrocarbon fraction (boiling point in the diesel-range) and a heavy stabilized hydrocarbon fraction (boiling point generally in the gas oil range). The heavy stabilized hydrocarbon fraction is recycled back to the pyrolysis reactor to facilitate the thermochemical conversion of biomass. The other fractions are sent to refinery for further processing into transportation fuels or directly blended with petroleum blendstocks to produce a liquid transportation fuel.

Certain embodiments recycle the heavy stabilized hydrocarbon fraction of the stable low-oxygen hydrocarbon products to the pyrolysis reactor. The separated heavy stabilized hydrocarbon fraction predominantly comprises hydrocarbons possessing a boiling point of 321° C. or greater, and typically includes hydrocarbons having a boiling point in the range of a gas oil (approximately 321° C.-566° C.) One advantage of the present systems and processes is that recycling of a heavy fraction of the upgraded products to the pyrolysis reactor reacts with the primary pyrolysis vapors prior to produce less reactive intermediate product vapors that are less likely to form coke on the at least one upgrading/hydrostabilizing catalyst in the upgrading/hydrostabilizing reactor.

In certain embodiments, the heavy stabilized hydrocarbon fraction contains constituent molecules that boil above 321° C. In certain embodiments, the boiling point of at least 90 wt % of hydrocarbon molecules in the heavy stabilized hydrocarbon fraction is greater than 343° C., alternatively greater than 370° C. In certain embodiments, the boiling point of at least 90 wt % of hydrocarbon molecules in the heavy stabilized hydrocarbon fraction is in the range between 343° C. and 566° C., alternatively in the range between 350° C. and 500° C.

Once recycled to the pyrolysis reactor, the hydrocarbons in the heavy stabilized hydrocarbon fraction undergo thermal cracking in the pyrolysis reactor. This produces hydrogen-rich intermediates that react with the nascent pyrolysis vapors produced from the biomass feedstock in the pyrolysis reactor. This produces stabilized pyrolysis vapors by eliminating highly reactive biomass pyrolysis intermediates and preventing detrimental secondary reactions that could prevent further upgrading/hydrostabilizing of the pyrolysis vapors. Recycling of a heavy stabilized hydrocarbon fraction may serve to decrease or eliminate a need for outside sources of hydrogen during hydropyrolysis in the pyrolysis reactor, as well as decrease the quantity of hydrogen that is required to be added to the upgrading/hydrostabilizing reactor. Recycling the heavy stabilized hydrocarbon fraction improves the quality of the pyrolysis vapors (by decreasing reactivity and/or partially deoxygenating the vapors) to allow easier upgrading/hydrostabilizing of the vapors ex-situ in the downstream upgrading/hydrostabilizing reactor.

Examples of biomass feedstock used in the present invention include, but are not limited to lignocellulosic biomass and oil-containing biomass, such as jatropha plant, macroalgae or microalgae. Carbohydrate-based biomass may also be used as feedstock, where carbohydrate-based refers to biomass where at least a fraction of its composition is made of carbohydrates. Carbohydrate-based biomasses are available from a variety of sources including cellulosic biomass and algal biomass. Specific examples of feedstock useful in the current invention include, but are not limited to: sugars, carbohydrates, fatty acids, proteins, oils, eucalyptus oil, forest residues, dead trees, branches, leaves, tree stumps, yard clippings, wood chips, wood fiber, sugar beets, *miscanthus*, switchgrass, hemp, corn, corn fiber, poplar, willow, sorghum, sugarcane, palm oil, corn syrup, algal cultures, bacterial cultures, fermentation cultures, paper manufacturing waste, agricultural residues (e.g., corn stover, wheat straw and sugarcane bagasse), dedicated energy crops (e.g., poplar trees, switchgrass, and *miscanthus giganteus* sugarcane) sawmill and paper mill discards, food manufacturing waste, meat processing waste, animal waste, biological waste and/or municipal sewage.

Lignocellulosic biomass primarily comprises cellulose, hemicellulose and lignin. These three components have structural differences that lead to different rates of pyrolysis. Hemicellulose comprises various sugars (xylose, mannose, glucose, galactose, etc.) connected into a relatively random, highly branched, amorphous structure. Hemicellulose pyrolysis requires relatively mild conditions from about 220° C. to about 315° C. with about 20 wt. % remaining as char. Cellulose comprises many long polymers of glucose that are relatively unbranched. It has a high degree of structural order and possesses good thermal stability. Yang, et al. further demonstrated that cellulose pyrolysis occurs predominantly at a higher temperature range from about 315° C. to about 400° C., with only about 6 wt. % remaining as char. Lastly, lignin possesses a high degree of thermal stability due to its high molecular weight, highly aromatic and cross-linked structure and thus, is more resistant to pyrolysis than cellulose or hemicellulose. Yang et al. found that cellulose and hemicellulose are both nearly completely pyrolyzed at 380° C., yet only around 20% of lignin is pyrolyzed at this temperature. Lignin pyrolysis was found to occur at a slower rate, yet this rate accelerated significantly at temperatures exceeding 400° C.

Lignocellulosic biomass is processed to particles prior to being fed into the pyrolysis reactor at a temperature that is typically less than 50° C. In preferred embodiments, the carrier or carrier gas within the pyrolysis reactor facilitates mixing of the lignocellulosic biomass with a heated solid particulate heat carrier, which rapidly heats the feedstock, resulting in at least partial pyrolysis of the feedstock by predominantly volatilizing the cellulose and hemicellulose components to a gaseous product comprising condensable pyrolysis vapors and un-condensable light gases. Particulate heat carriers are conventional in the art and composition will not be discussed further here however, to reduce particle entrainment leading to heat carrier exiting the reactor, the median heat carrier particle size is greater than about 100 microns, and preferably greater than about 250 microns. For similar reasons, the bulk density of the heat carrier particles is at least 500 kg/m$^3$, and preferably greater than about 1,000 kg/m$^3$.

Hydrodeoxygenation (HDO) of pyrolysis vapors is highly exothermic and releases an enormous amount of heat. Thus, conventional processes that utilize a fixed bed of hydrodeoxygenation catalyst have inherent difficulty dissipating excess heat from the catalyst bed due to the close packing of the catalyst in the fixed bed. This can result in an increased rate of catalyst deactivation via coking, and/consequent plugging of the catalyst bed.

Conventional processes typically upgrade hydropyrolysis vapor with a fixed bed hydrotreating reactor. Petroleum hydroprocessing technologies mainly use fixed bed reactors or, in few cases, ebulliated bed reactors. These reactors are good for petroleum feedstocks that normally contain less than 10 wt % of heteroatoms (O, S, N, etc.). However, the hydropyrolysis intermediates from biomass contain more than 30 wt % of oxygen and a large percentage of unsaturated C—C bonds. Removing these oxygen and saturation these double bonds releases a much larger amount of heat. This excessive heat is extremely difficult to dissipate from a fixed bed reactor. Consequent over-reacting and local over-heating rapidly deactivates the beginning portion of the fixed bed reactor and eventually plugs the reactor. The inventive processes and systems disclosed herein provide a reactor comprising a fluidized bed of at least one upgrading/hydrostabilizing catalyst that manages heat and mass transfer more efficiently for exothermic reactions, thereby extending catalyst lifetime.

The conditions and the catalyst(s) utilized in the fluidizing upgrading/hydrostabilizing reactor is(are) chosen to favor highly-selective cracking of C—O bonds of the oxygenates present in the pyrolysis vapors, while minimizing C—C bond breakage. The result is an increased yield of longer chain hydrocarbons versus conventional hydrodeoxygenation (HDO) conducted in a fixed-bed configuration, with the product being better-suited for use as a component of a liquid hydrocarbon transportation fuel. Simultaneously, the high hydrogenation activity resulting from the present methods and systems minimizes formation of coke on the catalyst surface and extends the life time of the upgrading/hydrostabilizing catalyst. The catalysts utilized in the inventive methods and systems disclosed herein can last much longer than typical zeolite-based upgrading/hydrostabilizing systems and processes to the point that a regenerator is not needed in certain embodiments.

Table 1 (below) demonstrates the highly-selective deoxygenation efficiency typical of the methods and systems disclosed herein characterized by selective cracking of C—O bonds in the oxygenates present in the pyrolysis vapors. The yield of deoxygenated C5+ hydrocarbons was typically higher than 90% (by carbon), while the yield of light hydrocarbons (i.e., C1-C4) resulting from cracking of C—C bonds was less than 5% (by carbon). In sharp contrast, the yield of deoxygenated C5+ hydrocarbons utilizing a zeolite catalyst (ZSM-5) was only 21.9% by carbon), while the cracked light yield was as high as 33.4% (by carbon). In the meantime, hydrogen partial pressure is critical to the selective cracking of C—O bonds. The table also shows a negative impact on the selective deoxygenation efficiency when hydrodeoxygenation was conducted at atmospheric pressure (1 atm) even when HDO catalyst.

TABLE 1

Comparing different deoxygenation chemistries

| | Embodiment of Present Invention | Conventional Catalytic Pyrolysis I | Conventional Catalytic Pyrolysis II |
|---|---|---|---|
| Catalyst | NiMo (supported) | ZSM-5 | CoMo (supported) |
| Pressure (psig) | 300 | 14.7 | 14.7 |
| Hydrogen Added? | Yes | No | Yes |
| Feedstock | Red Oak | Red Oak | Red Oak |
| Relative Yield | | | |
| Upgradable Organics | 100.0% | 100.0% | 100.0% |
| Deoxygenated C5+ Yield | 93.1% | 33.4% | 49.9% |
| Light HC Yield (C1-C4, $CO_x$) | 4.3% | 33.4% | 49.9% |
| Coke Yield | 2.6% | 44.7% | 13.4% |

Another advantage of the present system and methods that performs ex situ upgrading/hydrostabilizing of pyrolysis vapors in a separate reactor is that the operating conditions of temperature and hydrogen partial pressure can be selected independently for each of 1) the pyrolysis reactor and 2) the upgrading/hydrostabilizing reactor. This allows pyrolysis conditions (e.g., temperature, pressure, hydrogen partial pressure and/or heavy stabilized hydrocarbon recycle rate, residence time, etc.) to be tailored to the given biomass feedstock utilized, while simultaneously maximizing the yield of deoxygenated C5+ hydrocarbons by operating the upgrading/hydrostabilizing/stabilization reactor under potentially different operating conditions, depending upon the properties of the pyrolysis vapors, the catalyst utilized and the level of deoxygenation required to achieve a stable product. Through these improvements, the quality and yield of product suitable for use as a co-feed for a conventional refinery process, liquid transportation fuel, or a blend component thereof can be improved.

Upgrading/hydrostabilizing/stabilization of the pyrolysis vapors produces a product comprising C5+ hydrocarbons that are largely deoxygenated. In certain embodiments, the remaining oxygen content ranges from 10 wt. % to 1 wt %, alternatively from 5 wt % to 0.5 wt %, alternatively from 3 wt % to 0.2 wt %, alternatively from 1 wt. % to 0.2 wt %, alternatively less than 10 wt %, alternatively less than 5 wt % percent, alternatively less than 2 wt %, alternatively less than 1 wt %, alternatively less than 0.5 wt %. In certain embodiments, the remaining content of product molecules comprising at least one aldehyde functional group is less than 0.1 wt %, alternatively less than 0.05 wt. %, alternatively undetectable by conventional methods. In certain embodiments, the remaining content of product molecules comprising at least one carboxylic acid functional group is less than 0.1 wt %, alternatively less than 0.05 wt. %, alternatively undetectable by conventional methods. In certain embodiments, the remaining content of product molecules comprising at least one aldehyde functional group or at least one phenol group is undetectable by conventional methods, while the remaining oxygen content ranges from 10 wt % to 1 wt %, alternatively from 5 wt % to 0.5 wt %, alternatively from 3 wt % to 0.2 wt %, alternatively from 1 wt. % to 0.2 wt %, alternatively less than 10 wt %, alternatively less than 5 wt % percent, alternatively less than 2 wt %, alternatively less than 1 wt %, alternatively less than 0.5 wt %. In such embodiments, despite a remaining oxygen content that may be as much as 10 wt %, the liquid hydrocarbon product is thermally stable and can be stored for an extended period of several months or more prior to transportation of the liquid product, further processing of the liquid product in a refinery to produce a liquid transportation fuel component, or both. In the present disclosure, thermally stable is defined as no significant increase in viscosity or significant decrease in the upgradability of the resulting pyrolysis product.

This is in stark contrast to conventional pyrolysis oils, which are highly unstable, or even certain partially-deoxygenated pyrolysis oil products produced by biomass pyrolysis with in situ catalytic upgrading/hydrostabilizing. In certain embodiments, the liquid hydrocarbon product of the present inventive processes and systems may be stored for longer than 7 days, alternatively longer than 30 days, alternatively longer than 90 days, alternatively longer than 180 days without detrimental effects on the viscosity or upgradability of the liquid hydrocarbon product.

Table 2 details the properties of a typical liquid hydrocarbon product produced by the processes and systems disclosed herein utilizing two different catalysts. The table shows typical yields of carbon oxides (COx), light gases (C1-C4 HC), hydrocarbons of C5 or larger (C5+HC). C5+HC yields are higher than 40 C %. Oxygen content is adjustable. The liquid products can be distilled due to high thermal stability.

TABLE 2

Process yields and liquid products

| | NiMo | CoMo |
|---|---|---|
| Product Yields (Carbon %) | | |
| COx | 10.4 | 11.2 |
| C1-C4 HC | 18.7 | 13.2 |
| C5+ HC | 42.1 | 46.7 |
| Aqueous | 2.4 | 1.4 |
| Coke | 1.7 | 4.2 |
| Pyrolysis Char | 24.7 | 23.2 |
| Liquid Composition (wt %) | | |
| C | 84.2 | 77.0 |
| H | 10.3 | 9.6 |
| O | 5.4 | 13.4 |
| Liquid BP Range (wt %) | | |
| 0-430"F. | 74.6 | 55.0 |
| 430-650"F. | 20.6 | 33.3 |
| 650-1000"F. | 4.7 | 8.3 |

The separated light product hydrocarbons can be stored, transported or further-processed in a refinery to produce liquid hydrocarbon transportation fuels. The light product hydrocarbons typically have a boiling point that is less than 193° C. In certain embodiments, the light product hydrocarbons a have a boiling point that is less than 166° C. In certain embodiments, the light product hydrocarbons a have a boiling point ranging from 25° C. to 193° C., alternatively ranging from 25° C. to 166° C.). The light product fractions are at least partially deoxygenated, but more importantly, have extremely low reactivity and are capable of long-term storage in liquid form at atmospheric pressure. Further, the light product fractions can be reheated and/or further processed in a refinery (alone or as a co-feed with conventionally produced petroleum-derived hydrocarbons) without inducing coking of catalysts and/or process equipment. The light hydrocarbon product is preferably within the known boiling point range for gasoline, #2 diesel, jet fuel, or any combination thereof.

The light stabilized hydrocarbon fraction typically comprises hydrocarbons possessing a boiling point that ranges from 25° C. to 193° C., alternatively ranging from 0° C. to 166° C. The medium stabilized hydrocarbon fraction typically comprises hydrocarbons possessing a boiling point that ranges from 193° C. to about 321° C. Both the light and medium stabilized hydrocarbon fractions are at least partially-deoxygenated, but more importantly, have extremely low reactivity and are capable of long-term storage in liquid form at atmospheric pressure. Further, these light and medium stabilized hydrocarbon fractions can be reheated and/or further processed in a refinery (alone or as a co-feed with conventionally produced petroleum-derived hydrocarbons) without inducing coking of catalysts and/or process equipment. The light stabilized hydrocarbon product is preferably within the known boiling point range for gasoline, while the medium stabilized hydrocarbon fraction is preferably within the known boiling point range for #2 diesel, jet fuel, or any combination thereof.

In certain embodiments, the heavy stabilized hydrocarbon fraction of the upgraded hydrocarbon product is recycled to the pyrolysis reactor, where it mixes with the biomass feedstock and serves as a source for hydride transfer to the oxygenated intermediates produced by thermal cracking reactions that occur in the pyrolysis reactor. The effect of this hydride transfer is to quench reactive functional groups that can lead to uncontrolled oligomerization or coking. In the pyrolysis reactor, (in presence of added hydrogen gas) to lower oxygen content of the pyrolysis vapor and increased yield of upgradeable pyrolysis. Less hydrogen needed due to presence of heavy recycled co-feed.

Chemistry in the second upgrading/hydrostabilizing reactor is predominantly HDO. Decarboxylation or decarbonylation is avoided by choice of catalyst, temperature and pressure to selectively crack C—O bond (close to 90%) as opposed to C—C (10%)—9:1 ratio.

The combination of more stable (lower oxygen content) raw pyrolysis vapors and the temp and pressure conditions utilized in the hydrodeoxygenation reactor lead to much lower coking rate of the catalyst in the fluidized HDO reactor, eliminating the need for periodic catalyst regeneration (such as in NREL system, for example).

In the present methods and systems, far less supplemental hydrogen is required for hydrodeoxygenation of the pyrolysis product, which significantly lowers process cost. Further, conventional systems rely on non-specific catalysts that produce more CO and CO2, that is then water-gas shifted to produce the hydrogen required to support hydrotreating. The stabilized hydrocarbon products produced by the inventive processes are unique and more stable (lower O2) and contain less reactive groups. Further the present processes and systems are able to provide a stabilized product in a single upgrading/hydrostabilizing step, while prior conventional methods require additional processing (i.e., hydrotreating) prior to utilizing the product as a co-feed to a conventional refinery process.

The physical distance between the pyrolysis reactor and the upgrading/hydrostabilizing catalyst(s) contained within the upgrading/hydrostabilizing reactor may vary, but is preferably minimized, taking into consideration the space velocity of the primary gaseous product (optionally in a mixture with a carrier gas) out of the pyrolysis reactor. Minimizing this distance assists in decreasing the time between production of the primary gaseous product and subsequent contacting with one or more upgrading/hydrostabilizing catalyst(s). Through optimizing the variables of distance and space velocity, the current invention assures that the upgrading/hydrostabilizing catalyst sees primary products from pyrolysis and not secondary products created by reactions occurring after pyrolysis. Generally, the distance between the pyrolyzer and the upgrading/hydrostabilizing catalyst(s) is less than 4 ft. More preferably, this distance is less than 1 ft., and most preferably, less than 6 inches.

Optionally, the disengagement zone between the pyrolyzer and the upgrading/hydrostabilizing reactor comprising at least one upgrading/hydrostabilizing catalyst may include additional features to limit reactivity of the primary gaseous product prior to contact with the upgrading/hydrostabilizing catalyst(s). These may include (but are not limited to) temperature control, introduction of a gas or fluid to quench the primary gaseous product (as mentioned previously), flow control through judicious choices in geometry (preferably, a geometry minimizing bends and small orifices to decrease the potential for vapor condensation at the interface between reactors.

Figure 1:
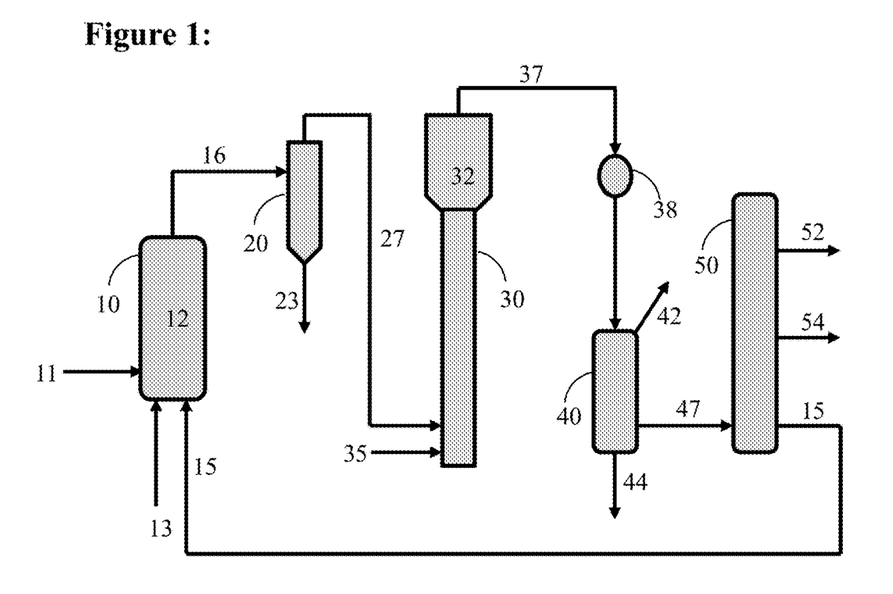
FIG. 1 is a simplified diagram intended to illustrate the general organization of one embodiment of the inventive processes and systems. The figure is not drawn to scale, and is elements.

One of many embodiments of the present inventive processes and systems is shown in FIG. 1. In the embodiment depicted in FIG. 1, a feedstock 11 comprising biomass is fed to a pyrolysis reactor 10 that is configured to maintain conditions of temperature (from about 300° C. to about 650° C.) and pressure (up to 400 psig) that facilitate pyrolysis of the feedstock. The pyrolysis reactor 10 optionally comprises a bed of a heat carrier 12 comprising solid particulates that is heated to a temperature that facilitates rapid transfer of heat from the heat carrier to the feedstock, thereby facilitating pyrolysis of the feedstock. Pyrolysis of the feedstock forms a gaseous pyrolysis product (not depicted) that, in turn, comprises non-condensable light gases and condensable pyrolysis vapors, and char (not depicted).

The embodiment depicted in FIG. 1 further depicts a carrier gas 13 that enters the pyrolysis reactor 10 at one or more entry points that are configured to allow the carrier gas 13 to perform one or more of: a) fluidize the feedstock 11 and heat carrier 12; b) assist in moving a mixture comprising condensable pyrolysis vapors, non-condensable light gases and char out of the pyrolysis reactor 10; c) react with the produced pyrolysis vapors to decrease reactivity and coke formation, and d) separate the char from the heat carrier 12 due to density difference, while entraining char in the carrier gas 13 and condensable pyrolysis vapors leaving the pyrolysis reactor 10.

The embodiment described in 1 further comprises at least one inlet for a recycled heavy stabilized hydrocarbon fraction 15. This heavy stabilized hydrocarbon fraction is a stable fraction that is recycled from the process (described in greater detail later) in order to facilitate the pyrolysis of the biomass feedstock within the pyrolysis reactor.

As mentioned, char that is entrained in the mixture 16 leaving the pyrolysis reactor 10 is separated from the mixture 16 by a cyclone 20 and eliminated via an outlet 23. A cleaned mixture 27 comprising non-condensable light gases and condensable pyrolysis vapors flows into an upgrading/hydrostabilizing reactor 30 containing at least one catalyst 32 (such as, for example, a hydrotreating catalyst on a fluidizable solid support) in a fluidized bed configuration. The catalyst 32 is preferably suitable for catalytically converting the oxygenated hydrocarbons present in the condensable pyrolysis vapors to an upgraded/stabilized product 37 consisting of at least one member selected from: a liquid hydrocarbon transportation fuel, a component thereof and a co-feed for a conventional refinery process.

The upgrading/hydrostabilizing reactor 30 optionally receives an input of hydrogen gas 35 to assist the catalytic upgrading/hydrostabilizing of the condensable pyrolysis vapors. However, in such embodiments, the quantity (partial pressure) of hydrogen 35 that must be added to the upgrading/hydrostabilizing reactor 30 is decreased or offset by the recycling of the heavy stabilized hydrocarbon fraction 15 to the pyrolysis reactor 10.

The embodiment depicted in FIG. 1 further comprises a conventional heat exchanger 38 that cools the upgraded/stabilized product 37 just upstream from separator 40. Separator 40 serves to remove water 44 from the upgraded/stabilized product 37 to produce a dewatered upgraded/stabilized product 47. In addition, non-condensable gases are removed from the separator 40 via an outlet 42 and may optionally be combusted for process heat. The process and system depicted in FIG. 1 additionally comprise a fractionation device 50 that may be any conventional device configured to fractionate hydrocarbon vapors by boiling point. The fractionator separates the dewatered upgraded/stabilized product 47 to produce a light stabilized hydrocarbon fraction 52 comprising molecules that boil in the range from about 25° C. to about 193° C., a medium stabilized hydrocarbon fraction 52 comprising molecules that boil in the range from about 193° C. to about 321° C. and the previously-mentioned heavy stabilized hydrocarbon fraction 15 that is recycled to the pyrolysis reactor.

The following examples of certain embodiments of the invention are given. Each example is intended to illustrate a specific embodiment, but the scope of the invention is not intended to be limited to the embodiments specifically disclosed. Rather, the scope is intended to be as broad as is supported by the complete disclosure and the appending claims.

Example 1

We investigated the recycling a heavy hydrocarbon fraction to the pyrolysis reactor in order to improve the yield of upgradeable pyrolysis vapors. We further examined whether co-pyrolysis of biomass and a heavy hydrocarbon fraction would help stabilize the highly reactive biomass pyrolysis intermediates (possibly through hydrocarbon thermal cracking and hydride transfer) and prohibit secondary reactions, thereby improving the quality of the pyrolysis vapor as well as the yield of upgraded product vapors leaving the upgrading/hydrostabilizing hydrostabilization reactor.

Table 1 shows the advantages of recycling a heavy hydrocarbon fraction to the pyrolysis reactor, demonstrated by co-pyrolysis of a biomass feedstock in the presence of vacuum gas oil (VGO) Table 1 shows results from co-pyrolysis of red oak and VGO in a micro-pyrolyzer connected with a GC-MS. The experiments detected components in the pyrolysis vapors from mixture of red oak+VGO, red oak alone, and VGO alone. After subtracting VGO pyrolysis products from mixture products, the C5+ oxygenates in the vapor decreased by 39% in the presence of VGO, while the C5+ hydrocarbons increased by 67%. This indicates that heavy stabilized hydrocarbons helped to partially deoxygenate and stabilize the active species in the pyrolysis vapor, thereby facilitating subsequent upgrading/hydrostabilizing (as well as potentially extending catalyst lifetime by decreasing the rate of catalyst coking).

TABLE I

Effect of VGO on Red Oak Pyrolysis

| Product Components | Relative Intensity of Products (by GC-MS) | |
|---|---|---|
| | Red Oak | Red Oak with VGO |
| C5+ Oxygenates (%) | 100 | 61 |
| C5+ HC (VGO Products subtracted) | 100 | 167 |

An additional benefit of recycling a heavy stabilized hydrocarbon fraction (comprising mostly long chain paraffins) according to the methods and systems disclosed herein includes cracking molecules within the heavy fraction into smaller, hydrocarbon products to increase the effective yield of hydrocarbon products in the boiling point range of gasoline, #2 diesel or jet fuel.

Example 2

The upgrading/hydrostabilizing of pyrolysis vapors in a fluidized bed of catalyst was tested by contacting hot pyrolysis vapors (derived from biomass) with a fluidized bed of hydrodeoxygenation catalyst in a reactor. The pyrolysis vapors were formed by pyrolyzing a lignocellulosic feedstock in a pulsed-mode mini-pyrolyzer. The fluidized bed upgrading/hydrostabilizing reactor processed 60-120 g of biomass over the course of a 1-2 h run, generating sufficient products for analysis. Product vapors were analyzed including product quality, process yields, a lab-scale fluidized bed upgrading/hydrostabilizing reactor was designed and built.

Nitrogen gas was used to purge the biomass and to facilitate powder transport. The fluidization gas, which was one of hydrogen, nitrogen, or a mixture of the two, was fed into the bottom of the pyrolysis reactor. A 100 μm stainless steel (SS) frit was used as the gas distributor. The biomass was decomposed in the pyrolysis reactor, which consisted of a 1" OD stainless steel tube (18" long) and standard Swagelok fittings. Produced char/coke and entrained sand were separated from the pyrolysis vapor in the cyclone. The cleaned pyrolysis vapor was upgraded in the upgrading/hydrostabilizing reactor that was loaded with one or more fluidized catalyst(s). The upgraded, deoxygenated products flowed through another cyclone or filter and were then cooled by a tube-in-tube heat exchanger. Liquid products were condensed, collected, and separated from gaseous products. The system pressure was maintained by a back-pressure regulator. A small stream of the flue gas (20-40 sccm) was diverted to an Agilent 7890B gas chromatograph (GC) for analysis.

A red oak feedstock (particle size of 200-500 μm) was pyrolyzed to provide the pyrolysis vapors that were upgrading/hydrostabilizing in these experiments. The biomass feedstock contained 5.8 wt % moisture, 45.4 wt % C, and 6.1 wt % H. Ash content was less than 1 wt. %. The heat carrier in the pyrolyzer was acid-washed sand ranging in size from 100 to 300 μm. A commercial hydroprocessing catalyst, KF-860 (Albemarle Corporation) was used in the upgrading/hydrostabilizing reactor. The catalyst was ground and sieved to 100-300 μm to ensure good fluidization.

Fluidization tests were conducted to determine the proper fluidization regime. For each test, 25 g of sand, and 30 g of KF-860 catalyst were loaded into the pyrolysis reactor, and the upgrading/hydrostabilizing reactor, respectively. Biomass was fed to the pyrolysis reactor at a rate of 1 g/min. The pyrolysis and upgrading/hydrostabilizing reactors were held at 425° C. and 350° C., respectively. The system pressure was 300 psig. The hydrogen flow rate was set to ensure good fluidization based on the fluidization test results. During each run, the gaseous products leaving the upgrading/hydrostabilizing reactor were analyzed using an Agilent 7890B gas chromatograph.

Three experiments were conducted under the same conditions (detailed above). The materials balances were consistently maintained between 97% and 99%, indicating high system reliability.

Figure 2:
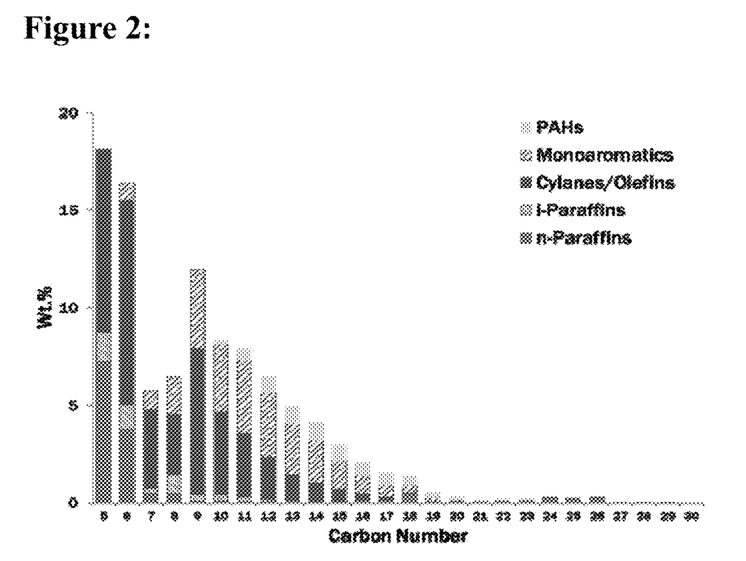
FIG. 2 is a graph showing a carbon-backbone size distribution of hydrocarbon products resulting from fluidized upgrading/hydrostabilizing of pyrolysis vapors, representative of one embodiment of the inventive processes and systems.

FIG. 2 shows a distribution of major products from the experiments. The carbon yields are averages of three runs. The small standard deviations indicate good data repeatability. It appears that of all the carbon in the feed, about 10% was converted to CO and CO2, 18.3% was in the form of C1-C4 light hydrocarbons, 41.2% was contained in C5+ liquid, and 28.6% was in the form of char or coke. These carbon yields added up to 98.2%. The C5+ liquid was identified to contain 84.4 wt % carbon, 10.4 wt % hydrogen, 5.2 wt % oxygen, and negligible amounts of nitrogen and sulfur. This liquid product was dramatically different from pyrolysis oil obtained from traditional pyrolysis (30-40 wt % oxygen) and catalytic pyoil (10-20 wt % oxygen) derived from a conventional catalytic pyrolysis process. The low oxygen content of the product produced by the fluidized upgrading/hydrostabilizing process was easier to upgrade and conducive to either storage or utilization as a feedstock (or co-feed) for a conventional refinery. Simulated distillation analysis showed that 50.3 wt % of the liquid boiled in the gasoline boiling point range, 40.6 wt % boiled in the diesel boiling point range, and 9.1 wt % is in the gas oil boiling point range. These composition data are summarized in Table 2 (see above).

Example 3

A detailed analysis was conducted of the C5+ hydrocarbon products generated from fluidized upgrading/hydrostabilizing of pyrolysis vapors produced by the fluidized pyrolysis of a lignocellulosic biomass, as detailed in Example 2. A distribution of hydrocarbon species was obtained and compared to the spectrum of chemical species present in conventional crude oil feedstock. The dominant molecular species were identified and used to elucidate possible chemical pathways utilized during the upgrading/hydrostabilizing of the pyrolysis vapors. The structures of oxygenates remaining in the upgraded product were also identified and quantified.

Figure 3:
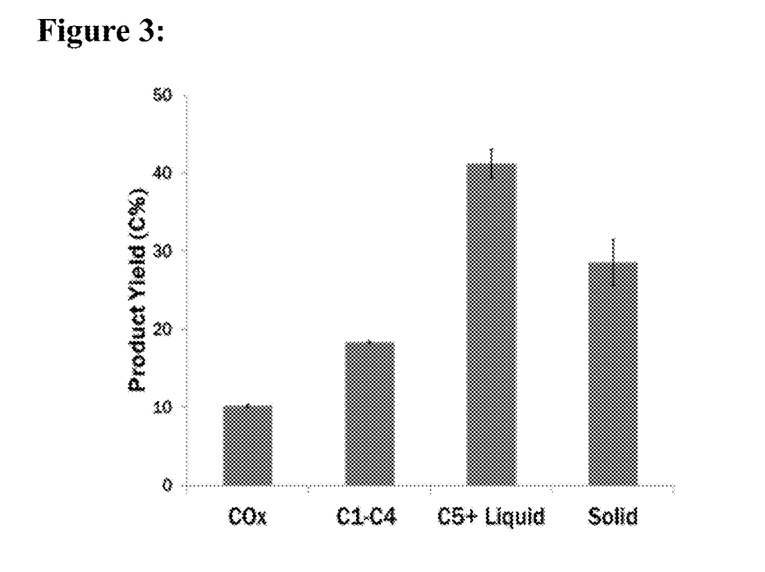
FIG. 3 is a graph showing the carbon-backbone size distribution of products from the fluidized upgrading/hydrostabilizing of pyrolysis vapors, representing one embodiment of the inventive processes and systems.

FIG. 3 shows the distribution of C5+ hydrocarbons in the products. The hydrocarbon size distribution was determined by combining NOISE (Nitric Oxide Ionization Spectrometry Evaluation) analysis of liquid products with gas chromatography (GC) analysis of gaseous products.

Regarding the types of hydrocarbons, the fluidized upgrading/hydrostabilizing products contained significantly less n-paraffins and iso-paraffins, which were narrowly distributed around C5 and C6. The products obtained by fluidized upgrading/hydrostabilizing were also rich in naphthenes and aromatics, especially in the C5, C6, and C9 families. The relatively high content of aromatics could boost the octane number for gasoline products.

The concentrated distribution of hydrocarbons product containing 5, 6, and 9 carbons raised interest in the nature of these compounds and possible chemical transformation during the fluidized upgrading/hydrostabilizing reaction. Detailed analysis through DHA (Detailed Hydrocarbon Analysis) and GC-MS allowed identification of pentane, hexane, cyclopentane, and cyclohexane as the dominant species in C5 and C6 products, and propylbenzene and propylcyclohexane as predominant in the C9 products.

Figure 4:
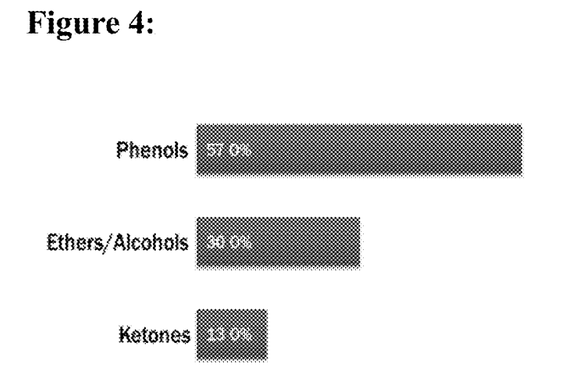
FIG. 4 is a graph showing the percentage of several functional groups remaining in a hydrocarbon product resulting from fluidized upgrading/hydrostabilizing of pyrolysis vapors.

The CHNS analysis determined that the C5+ hydrocarbon products from the fluidized upgrading/hydrostabilizing tests contained less than 5 wt. % of oxygen. A combination of GC-MS and NMR techniques enabled identification and quantification of remaining oxygenated hydrocarbons. As shown in FIG. 4, more than 50% of oxygen was in the form of phenols or substituted phenols, 30% as ethers/alcohols, and 13% as ketones. The dominant species in each category are 3-propylphenol, 2,5-dimethylfuran, and cyclopentanone, respectively.

Definitions

As used herein, the term "stabilized" is defined as any product of a chemical reaction that less chemically reactive and/or more resistant to thermal degradation, when compared to the starting material or feedstock.

As used herein, the term "entrainment" is defined as transport of a solid particle by a gas stream. Entrainment of a given solid particle typically occurs when the local velocity of a gas stream exceeds the terminal falling velocity of the particle.

As used herein, any reference to the term "standard gas hourly space velocity" or "SGHSV" refers to the gas hourly space velocity of a gas stream measured at standard conditions.

In closing, it should be noted that the discussion of any reference is not an admission that it is prior art to the present disclosure, in particular, any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

We claim:

1. A process for pyrolyzing biomass and upgrading/hydrostabilizing the vapors, comprising:
   a) pyrolyzing a feedstock that is derived from biomass in a first reactor for a residence time of less than 10 seconds in the absence of a catalyst and the presence of a heavy stabilized hydrocarbon fraction consisting of hydrocarbon molecules characterized by a boiling point (at 1 atm.) that is greater than 321° C., to produce a primary pyrolysis product comprising condensable pyrolysis vapors and char;
   b) conveying the condensable pyrolysis vapors to a second reactor containing hydrogen and at least one fluidized bed of at least one catalyst, and contacting the condensable pyrolysis vapors with the at least one catalyst at conditions of temperature that facilitate the production of a stabilized hydrocarbon product, wherein the stabilized hydrocarbon product comprises hydrocarbons having less than 0.1 wt. percent aldehyde functional groups and less than 0.1 wt percent carboxylic acid functional groups;

c) fractionating the stabilized hydrocarbon product to produce the heavy stabilized hydrocarbon fraction of a), and fuel-range stabilized hydrocarbons characterized by a boiling point ranging from between 25° C. and 321° C.

2. The process of claim 1, wherein the fuel-range stabilized hydrocarbons comprises a light stabilized hydrocarbon fraction characterized by a boiling point ranging from between 25° C. and 193° C., and a medium stabilized hydrocarbon fraction characterized by a boiling point ranging from between 193° C. and 321° C.

3. The process of claim 1, wherein the boiling point of at least 90 wt % of hydrocarbon molecules in the heavy stabilized hydrocarbon fraction is greater than 343° C.

4. The process of claim 1, further comprising co-feeding the light stabilized hydrocarbon fraction, the medium stabilized hydrocarbon fraction, or both, with petroleum-derived hydrocarbons to a refinery process.

5. The process of claim 1, further comprising condensing and storing the light stabilized hydrocarbon fraction, the medium stabilized hydrocarbon fraction, or both, for a period in excess of seven days prior to use.

6. The process of claim 1, wherein the fractionating of c) comprises selective condensation of the heavy stabilized fraction.

7. The process of claim 1, further comprising blending the light stabilized hydrocarbon fraction, the medium stabilized hydrocarbon fraction, or both, with conventional petroleum-derived hydrocarbons to produce a finished liquid transportation fuel.

8. The process of claim 1, wherein recycling of the heavy stabilized hydrocarbon fraction to the pyrolysis reactor decreases the partial pressure of hydrogen required in the second reactor by at least 50 psig.

9. A system for the production and upgrading/hydrostabilizing of a stabilized pyrolysis product, comprising:
  a. a pyrolysis reactor that does not contain a catalyst and that is configured to fluidize and rapidly pyrolyze a feedstock comprising biomass for a residence time of between 1 and 20 seconds to produce a gaseous product comprising non-condensable light gases, condensable pyrolysis vapors, and char, wherein the pyrolysis reactor comprises:
    a first inlet configured to receive a stabilized heavy hydrocarbon fraction comprising stabilized hydrocarbons that are characterized by a boiling point greater than 350° C.,
    a second inlet configured to receive the biomass feedstock,
    at least one outlet configured to remove the gaseous product from the reactor,
    at least one inlet configured to receive a carrier gas and operable to fluidize the feedstock;
  b. a second reactor containing at least one catalyst in a fluidized bed configuration, wherein the second reactor is configured to receive the gaseous product and maintain a temperature and pressure that facilitate the catalytic conversion of the condensable pyrolysis vapors to produce a stabilized hydrocarbon product;
  c. a fractionation device configured to separate the stabilized hydrocarbon product to produce a heavy stabilized hydrocarbon fraction, the fractionation further comprising an outlet for the heavy stabilized hydrocarbon fraction;
  d. a conduit operably connected to receive the heavy stabilized hydrocarbon fraction and convey it to the pyrolysis reactor.

10. The system of claim 9, wherein the pyrolysis reactor additionally contains a fluidizable bed of a heat carrier, the heat carrier comprising a particulate solid.

11. The system of claim 9, wherein the pyrolysis reactor is configured to pyrolyze the biomass feedstock at a temperature in the range from 300° C. to 650° C. and for a residence time of less than 10 sec.

12. The system of claim 9, wherein the second reactor comprises a fluidized bed of at least one upgrading/hydrostabilizing catalyst, wherein the second reactor is configured to catalytically convert the condensable pyrolysis vapors to produce a stabilized hydrocarbon product that is a member selected from the list consisting of: a co-feed for a conventional refinery process, a liquid hydrocarbon transportation fuel or a component thereof.

13. The system of claim 9, further comprising a separator that is directly coupled to the second reactor and configured to receive the stabilized hydrocarbon product from the second reactor and to remove water and flue gas from the stabilized hydrocarbon product to produce a dewatered stabilized hydrocarbon product.

14. The system of claim 9, further comprising a fractionation device that is directly coupled to the separator and configured to receive the dewatered stabilized hydrocarbon product from the separator, wherein the fractionation device is configured to receive and fractionate the dewatered stabilized hydrocarbon product into two or more fractions based upon boiling point, including the stabilized heavy hydrocarbon fraction.

\* \* \* \* \*